(12) United States Patent
Bencteux et al.

(10) Patent No.: US 10,149,728 B2
(45) Date of Patent: Dec. 11, 2018

(54) ELONGATE MEDICAL PART GUIDE MODULE

(71) Applicant: ROBOCATH, Rouen (FR)

(72) Inventors: Philippe Bencteux, Bois-Guillaume (FR); Sébastien Deboeuf, Herblay (FR); Jacques Marignier, Le Mesnil Esnard (FR)

(73) Assignee: ROBOCATH, Rouen (FR)

( * ) Notice: Subject to any disclaimer, the term of this patent is extended or adjusted under 35 U.S.C. 154(b) by 71 days.

(21) Appl. No.: 15/492,097

(22) Filed: Apr. 20, 2017

(65) Prior Publication Data
US 2017/0239004 A1 Aug. 24, 2017

Related U.S. Application Data

(62) Division of application No. 14/770,747, filed as application No. PCT/FR2014/050527 on Mar. 7, 2014, now Pat. No. 9,687,304.

(51) Int. Cl.
*A61B 34/30* (2016.01)
*A61M 25/01* (2006.01)
*A61B 90/00* (2016.01)

(52) U.S. Cl.
CPC ......... *A61B 34/30* (2016.02); *A61M 25/0113* (2013.01); *A61B 2034/301* (2016.02); *A61B 2090/376* (2016.02)

(58) Field of Classification Search
CPC ....................................................... A61B 34/30

USPC .................................................. 318/560, 34
See application file for complete search history.

(56) References Cited

U.S. PATENT DOCUMENTS

| 7,389,156 | B2 | 6/2008 | Ziegler et al. | |
|---|---|---|---|---|
| 7,620,476 | B2 | 11/2009 | Morse et al. | |
| 7,927,310 | B2 | 4/2011 | Bencteux | |
| 9,687,304 | B2 | 6/2017 | Bencteux et al. | |
| 2003/0176770 | A1* | 9/2003 | Merril | A61B 34/70 600/118 |
| 2006/0146010 | A1 | 7/2006 | Schneider | |
| 2012/0179167 | A1 | 7/2012 | Wenderow et al. | |

FOREIGN PATENT DOCUMENTS

EP 1 442 720 A1 8/2004
WO WO 2005/117596 A2 12/2005

* cited by examiner

*Primary Examiner* — David S Luo
(74) *Attorney, Agent, or Firm* — Miller, Matthias & Hull LLP

(57) ABSTRACT

The invention concerns a module for guiding an elongate medical part along an elongation axis for a robotic system comprising: mobile apparatus mounted so as to rotate relative to a base about a rotational axis, and defining a space for receiving the elongate medical part, and comprising a rotational guiding system comprising a passage region for the elongate medical part corresponding to the location of the passage of the elongate medical part through the mobile apparatus, and a plurality of rotary guiding portions distributed about the rotational axis, and access aperture comprising an angular aperture of at least 30°.

14 Claims, 12 Drawing Sheets

ELONGATE MEDICAL PART GUIDE MODULE

This is a divisional application under 35 U.S.C. § 121 claiming priority to U.S. patent application Ser. No. 14/770,747 filed on Aug. 26, 2015, which is a U.S. National Phase of International Application No. PCT/FR2014/050527 filed Jul. 3, 2014, which claims priority under the Paris Convention to French Patent Application No. FR 13 52062 filed on Mar. 7, 2013.

FIELD OF THE DISCLOSURE

The present invention relates to modules for driving robotic catheterization systems.

BACKGROUND TO THE DISCLOSURE

Manual insertion of a catheter into a patient is relatively standard surgery. However, as this procedure is performed with X-ray monitoring, the surgeon in charge of the procedure is exposed to substantial radiation when performing such operations on numerous patients.

To reduce the risk to the surgeon, such insertions can be automated using robots. Such automation is complex, because the act of holding the catheter is complex. The catheter is bathed in preservative liquid and must remain sterile. In addition, it should be possible to alternate between rotational and translational movements of the catheter. And of course these robotic systems must be completely reliable.

Recently, a drive system was proposed in U.S. Pat. No. 7,927,310 that manages both the translational and rotational movements of the catheter. The catheter is retained on a plate that rotates relative to a base in order to provide the rotation. The plate itself comprises a mechanism to provide the translation. In addition, there are external motors fixed to the frame, and systems for transferring motion to the catheter. It is preferred not to have embedded motors for reasons concerning power capacity, bulk, and sterility.

However, the problem remains of emergency removal of the catheter from the mechanism. We want to be able to uncouple the catheter from the mechanism as easily as possible when there is an emergency, allowing the physician to resume the operation manually. In the above document, because the catheter traverses closed passages, such uncoupling is not provided for. In addition, the possibility for uncoupling must not adversely affect the normal operation of the robot. In other words, it must not reduce the maneuverability or reliability of the robot.

The present invention is intended to overcome these disadvantages.

SUMMARY OF THE DISCLOSURE

To this end, the invention provides a module for driving an elongate medical part extending along an elongation axis, for a robotic system, comprising:
  a base carrying at least one rotation control member,
  a mobile apparatus mounted so as to rotate relative to the base about an axis of rotation, and defining a receiving space for the elongate medical part,
  the mobile apparatus comprising a rotation driving system comprising a passage region for the elongate medical part corresponding to the location for the passage of the elongate medical part through the mobile apparatus, and a plurality of rotation driving portions distributed about the axis of rotation, each suitable for cooperating with at least one rotation control member, the rotation driving portions being arranged, in a driving configuration, such that at least one of the rotation driving portions cooperates with at least one of the rotation control members regardless of the relative orientation of the mobile apparatus and the base about the axis of rotation,
  an access aperture extending from the receiving space between two adjacent rotation driving portions, and by which the elongate medical part is radially movable between a usage configuration where it extends into the receiving space, and an external configuration where it is external to the driving module, the access aperture having an angle of aperture of at least 30° measured as projected onto a plane normal to the axis of rotation between two straight lines extending from the passage region to each of the two adjacent driving portions in the access configuration.

In effect, to facilitate catheter removal from the mechanism, it is necessary to provide a withdrawal opening in the mechanism. This creates a system requiring very few operations to uncouple the catheter from the mechanism.

This is applicable to a catheter, but also to any type of appropriate elongate flexible medical part, such as a guide, an interventional catheter, etc.

In preferred embodiments of the invention, one or more of the following arrangements may possibly be used:
  the driving module further comprises a translation driving system for the elongate medical part, carried by the mobile apparatus, comprising at least one surface suitable for being placed in contact with the elongate medical part and suitable for being placed in motion relative to the mobile apparatus in order to drive the elongate medical part in translation along the elongation axis,
  said surface being further adapted for gripping the elongate medical part so as to rotate it about the axis of rotation;
  the mobile apparatus comprises a frame supporting at least one rotary member of the translation driving system, the rotation driving system being integral with the frame;
  the access aperture is a first access aperture, wherein the frame carries the translation driving system, the translation driving system comprising a passage region for the elongate medical part corresponding to the location for the passage of the elongate medical part through the mobile apparatus, and a plurality of translation driving portions distributed about the axis of rotation, each adapted to cooperate with at least one translation control member of the base,
  the translation driving portions being arranged, in the driving configuration, such that at least one of the translation driving portions cooperates with at least one of the translation control members regardless of the relative orientation of the mobile apparatus and the base about the axis of rotation,
  a second access aperture extending from the receiving space between two adjacent translation driving portions,
  the second access aperture having an angle of aperture of at least 30° measured as projected onto a plane normal to the axis of rotation between two straight lines extending from the passage region to each of the two adjacent driving portions in the access configuration;
  the translation control member cooperates with a shaft rotatable about a shaft axis of rotation, and having a cross-section in the shape of an arc of a circle centered on the axis of rotation whose central angle is greater than the angle of aperture of the second access aperture and less than 360° minus the angle of aperture of the second access aperture;

the first and second access apertures are superimposed in a projection normal to the axis of rotation, regardless of the relative orientation of the mobile apparatus and the base;

the rotation driving system comprises a connection portion, and at least two arms extending from both sides of the receiving space and each connected to the connection portion;

at least one, or possibly each, of the access apertures has an angle of aperture at least equal to 45° in the access configuration, or possibly at least equal to 90°;

the rotation control member comprises a belt that can be driven to travel a path along the base, said path comprising an arc portion of a circle centered on the axis of rotation and having a central angle greater than the angle of aperture and less than 360° minus the angle of aperture;

said rotation control member comprises a shaft rotatable about a shaft axis of rotation, and having a cross-section in the shape of an arc of a circle centered on the axis of rotation with a central angle greater than the angle of aperture of the access aperture and less than 360° minus the angle of aperture of the access aperture;

the mobile apparatus comprises a removable cap that is suitable:
  in the assembled position, for closing the access aperture and preventing radial movement of the elongate medical part between its usage configuration and its external configuration, and
  in the disassembled position, for opening the access aperture and enabling such movement;

the removable cap comprises a rotation driving surface that is suitable, in the assembled position, for cooperating with at least one rotation control member in the driving configuration;

the cap is retained on the mobile apparatus such that it is movable between the assembled configuration and the disassembled configuration;

the set of parts of the driving module is in the form of disposable and/or sterilizable elements (the disposable elements can be discarded after use and replaced with identical elements for future use, and the various non-disposable elements are parts that can be disassembled and sterilized for future use).

In another aspect, the invention relates to a module for driving an elongate medical part along an elongation axis, for a robotic system, comprising:

a base, carrying at least one rotation control member, a mobile apparatus mounted so as to rotate relative to the base about an axis of rotation, and defining a receiving space for the elongate medical part, the mobile apparatus comprising a rotation driving system adapted to cooperate with at least one rotation control member, regardless of the relative orientation of the mobile apparatus and the base about the axis of rotation, the mobile apparatus comprises a removable cap that is suitable:
  in the assembled position, for closing an access aperture to the receiving space and for preventing radial movement of the elongate medical part between its usage configuration and its external configuration, and
  in the disassembled position, for opening the access aperture and enabling such movement.

In particular, the cap supports a portion of the driving system according to the degree of freedom.

BRIEF DESCRIPTION OF THE DRAWINGS

Other features and advantages of the invention will be apparent from the following description of several of its embodiments, given by way of non-limiting example with reference to the accompanying drawings.

In the drawings.

In the various figures, the same references designate identical or similar elements.

DETAILED DESCRIPTION OF THE DISCLOSURE

Figure 1:
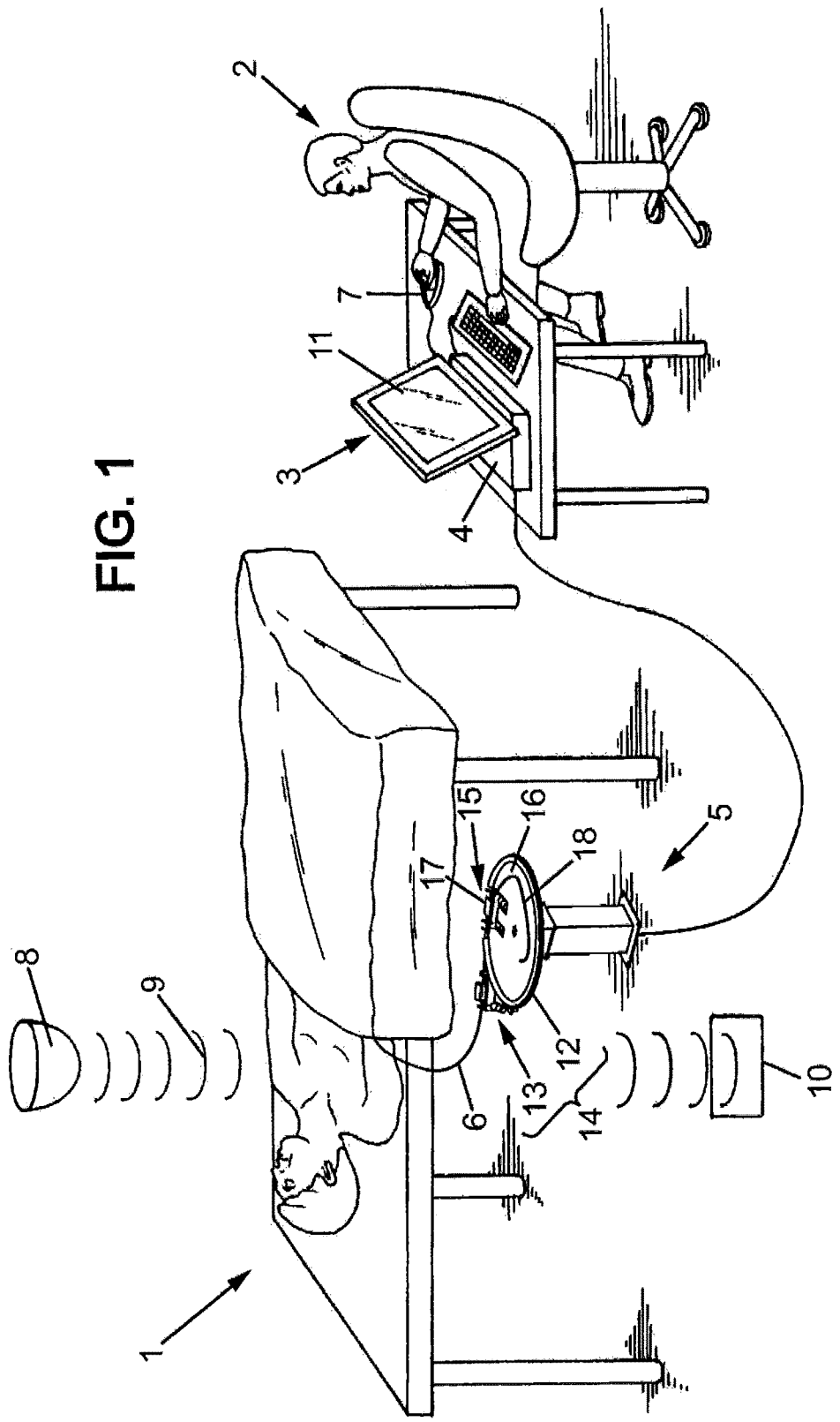
FIG. 1 illustrates an example system for robotic arteriography.

FIG. 1 illustrates an example of a medical system. A patient 1 is lying on an examination table, and the medical staff 2 is performing an automated catheterization. The catheterization is automated via a computerized unit 3 comprising a central processing unit 4 (processor, logic, or other) remotely controlling a robot 5. The robot 5 is able to move an elongate flexible medical part 6 inside the patient 1, under the control of the computerized unit 3. "Elongate flexible medical part" is understood to mean a flexible part that is longitudinally elongated and that can be inserted into a tubular passage of a patient, particularly an artery or vein of a patient, such as a catheter in the conventional sense of the term, a guide wire guiding such a catheter, an endoscope, an interventional catheter fitted with medical equipment such as a balloon, a gripping or surgical tool, etc.

The robot 5 can be controlled by the computerized unit 3 according to a predefined program, or by the medical staff 2 via a user interface 7 such as a mouse, keyboard, joystick, or similar device.

Such catheterization is monitored by imaging, in particular X-ray imaging. An X-ray source 8, 9 may therefore be provided, emitting an X-ray beam toward a patient, as well as an X-ray detector 10 arranged beyond the patient and able to detect transmission of the X-ray beam through the patient. The imaging system can be connected to the computerized unit 3 so that the image obtained by the imaging system is visible on the screen 11 of the computerized unit. Alternatively, the radiographic image is displayed on a dedicated screen. The medical staff 2 can thus control the catheterization while viewing on the screen 11 the position of the elongate flexible medical part within the patient in relation to the various organs of the patient, which allows controlling various movements of the elongate flexible medical part, by means of the robot 5, such as the two main movements which are tie longitudinal translation of the elongate flexible medical part in either direction (advancing or withdrawing) and/or the rotation of the elongate flexible medical part about its longitudinal axis (in either direction).

The robot 5 will be described in more detail below. The robot mainly comprises a receptacle 12 in which the elongate flexible medical part can be contained in a sterile manner. For example, the receptacle 12 is a tube open at one end, which contains the elongate flexible medical part immersed in a sterile liquid such as normal saline solution. The elongate flexible medical part exits through one end of the receptacle 12, and cooperates with a driving module 13 supported by the robot 5 and described in more detail below. The driving module 13 can receive two commands from the computerized unit 3: a command to move translationally along the longitudinal direction of the elongate flexible medical part, and a command to move rotationally about this direction. When appropriate, each command received by the robot comprises a combination of a translation command and a rotation command in different proportions, and a judicious combination of two commands allows, where necessary, ordering a purely translational movement or purely rotational movement of the elongate flexible medical part by simple resolution of mathematical equations.

Note that the robot 5 can be more complex if such is appropriate. In particular, the robot 5 can be used for controlling two medical devices such as an elongate flexible medical part (as described above) and a guide threaded inside the elongate flexible medical part. Thus the robot 5 comprises, in addition to the first system 14 described above comprising both the container 12 and the driving module 13, a second system 15 comprising a receptacle 16 and a driving module 17 for the medical device contained in the receptacle 16. Similarly, the second system 15 cooperates with the first 14, with the end of the second system 15 connected to the receptacle 12 of the first system 11, and more particularly to the back end of the elongate flexible medical part 6. Thus, the guide 18 can be moved within the elongate flexible medical part 6. Driving module 17 is similar to driving module 13, apart from the adaptation to the diameter of the part to be driven, and will not be specifically described. The robot 5 is controlled by the computerized unit 3 so that the driving module 17 controls the translation of the guide 18 in the longitudinal direction, and the rotation about this direction. The receptacle 16 is, for example, a basin for holding a preservative liquid for storing the guide 18. If necessary, a third system of a similar design (not shown) can be used, nested within the second.

Figure 2:
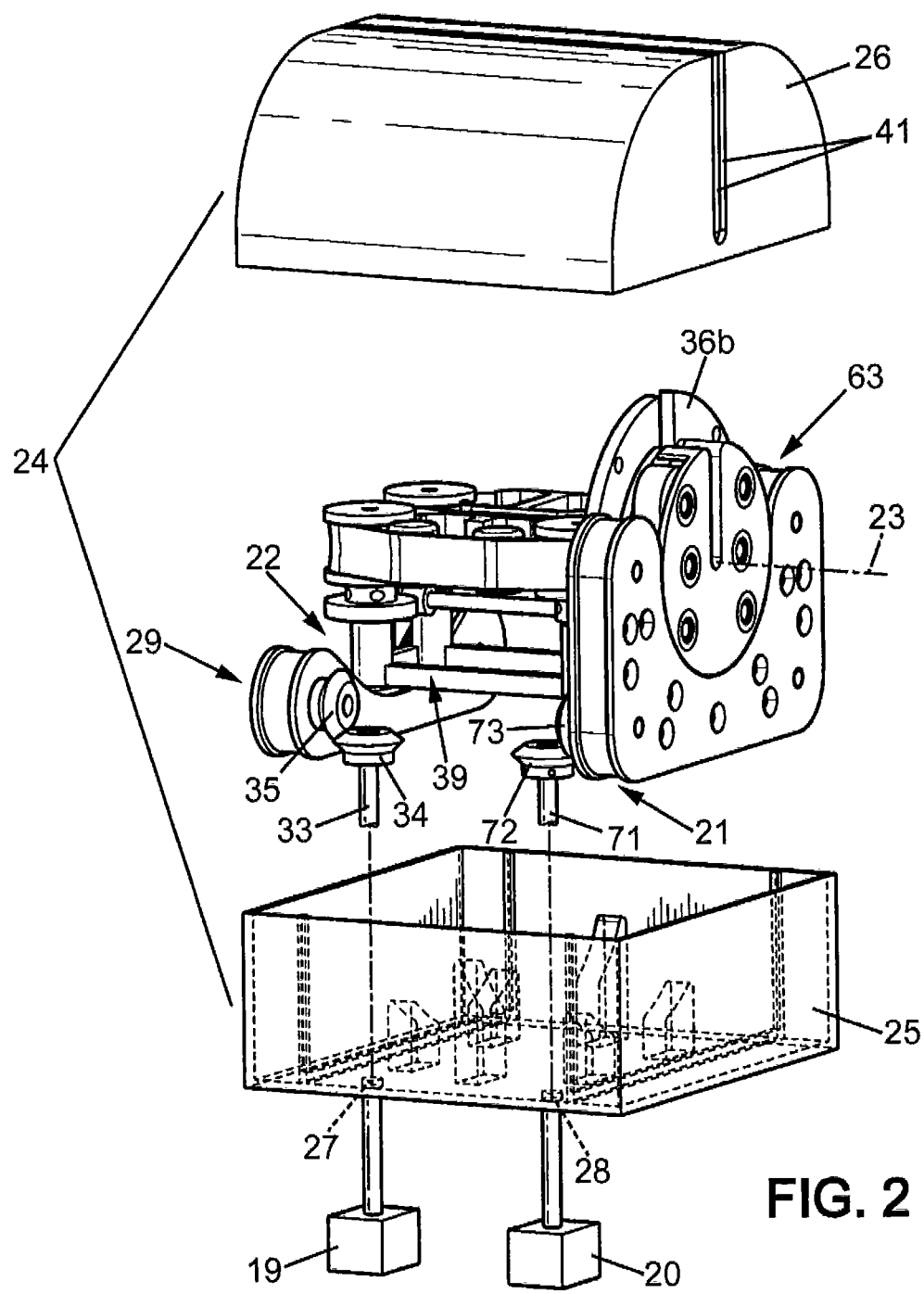
FIG. 2 is an exploded perspective view of a driving module according to a first embodiment.

A first example of a driving module 13 will be described with reference to FIG. 2. A distinctive feature of the driving module 13 is that it has no embedded motor. The motors are fixed and the motions to impart to the elongate flexible medical part are transmitted by a transfer system. Two motors 19 and 20 are thus provided, independently controllable by the computerized unit 3. Motor 19 controls rotation of the elongate flexible medical part 6. Motor 20 controls translation of the elongate flexible medical part 6.

Another distinctive feature of the driving module 13 is that a single module controls both the rotational and translational movements of the elongate flexible medical part. This is achieved in practice by providing a fixed base 21 for the driving module, integral to the motors 19 and 20. The fixed base supports a mobile apparatus 22 adapted to rotate about the base 21 about an axis 23 extending in the main direction. In this example, the axis 23 coincides with the longitudinal direction of the elongate flexible medical part to be driven. As will be explained in more detail below in various embodiments, the mobile apparatus supports a system 120 for gripping the elongate flexible medical part which possibly may not be driven, in which case the rotation of the mobile apparatus relative to the base causes rotation of the elongate flexible medical part about the main direction.

The driving module 13 comprises a housing 24 which receives the base 21 and the mobile apparatus 22, and provides basic protection from external contaminants. The housing 24 comprises a lower receptacle 25 and an associated cover 26. The receptacle 25 and the cover 26 can be associated (by fitting one inside the other or by some other means) to form a substantially closed space holding the base 21 and the mobile apparatus 22. The receptacle 25 comprises two passages 27 and 28 which can respectively be traversed by a rotation control shaft 33 and a translation control shaft 71, respectively connected to the rotation motor 19 and the translation motor 20.

The base 21 comprises part of a rotational movement control system 29. In particular, the rotational movement control system 29 imparts, to the mobile apparatus 22, a rotational movement about the axis 23. This system 29 is particularly visible in FIG. 7. In particular, according to this embodiment, the system 29 comprises a closed endless belt 30 movable along a path comprising a portion forming an arc 30', the center of the arc's circle coinciding with the axis 23. A guide system 31 guides the belt 30 along this path. A mechanical transfer system 32 is provided for driving the belt 30 along its path in particular, it may be arranged for example that the end of the rotation control shaft 33 comprises a gear 34 meshing with a gear 35 driving the belt 30. In particular, a mechanical transfer system 32 comprising a right-angle drive transfer may be provided.

The mobile apparatus 22 comprises a housing 39 extending between two end faces 36a (FIG. 7) and 36b (FIG. 3) along the main direction. The housing 39 is secured to a plate 90. The plate 90 comprises, for example, discrete driving surface portions 38a-d of a right circular cylinder about the axis 23, cooperating with the belt 30, and forming a rotation driving system 38. For this cooperation, it may be arranged for example that the belt 30 has a driving face, and that the discrete driving surface portions 38a-d have a complementary surface. The driving face of the belt and a driving surface portion 38a are in a driving relation such that movement of the belt 30 causes the housing 39 to rotate about the axis 23. The plate 90 thus comprises, in the example shown, four arms 91a-91d extending from a connection area 92. In the position shown, the connection area 92 is below the axis 23, and the arms extend substantially radially therefrom to a respective driving surface portion 38a-38d. Thus, the various pairings of the four driving surface portions define four peripheral open areas, each defining an angle of aperture of about 45° when projected onto a plane normal to the axis 23. As the connection area 92 is not central, the angle of aperture of the various open areas may vary. In particular, one of these open areas leads to the receiving space for the elongate medical part, and is called an access aperture 93. The elongate flexible medical part passes through the plate 90 via a passage region 105, indicated by dotted lines, which in this example extends around the axis 23. The access aperture 93 is defined by two straight lines D1 and D2, which when projected onto a plane normal to the axis 23, extend from the passage region 105 to each of the adjacent driving surface portions 38a, 38d. The access aperture 93 forms an angle of aperture of at least a $\alpha=30°$, possibly at least 45°, and can be up to 90°.

Note that two of the arms 91b and 91c of the plate 90 each have an attachment area 93b, 93c for attachment to the frame 43 of the housing, shown in phantom, which will be described in more detail below.

Referring again to FIG. 2, the housing 39 defines a receiving space 40 extending substantially between the two end surfaces 36a and 36b. In particular, the receiving space 40 extends continuously along the main direction. In particular, the receiving space 40 extends continuously with the access aperture 93 provided between the two adjacent discrete driving surface portions 38a, 38d. The receiving space 40 is sufficiently large to permit radial insertion or removal of an elongate flexible medical part 6 by means of said space between a usage configuration in which it is inserted into the receiving space and an external configuration where it is external to the module 13. Furthermore, two elastomer lips 41 may be provided on the cover 26 to close off access to the inside space 40, preventing contaminants from entering but deformable to allow inserting or removing an elongate flexible medical part between them.

Figure 5:
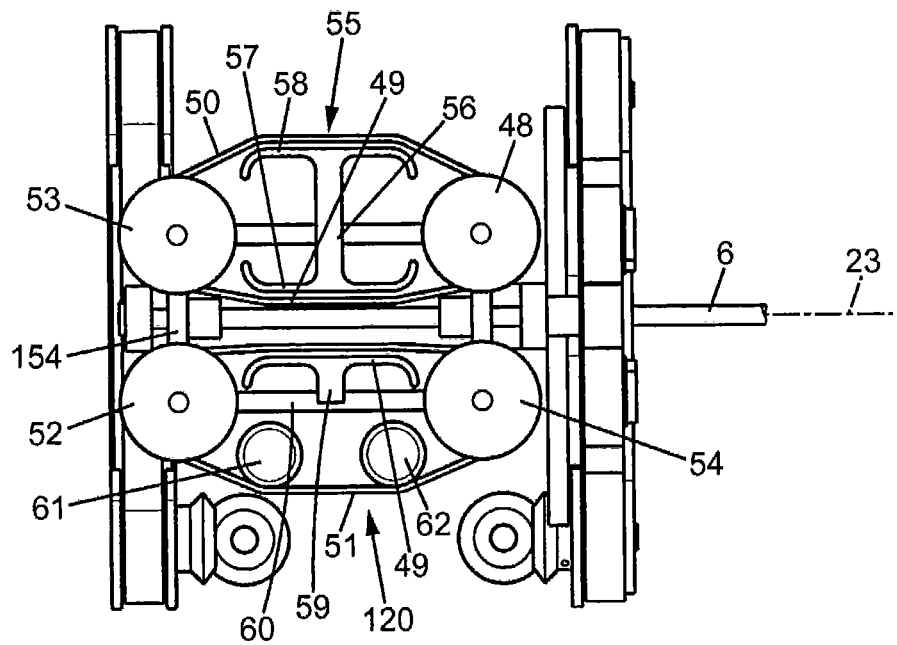
FIG. 5 is a top view of the system of FIG. 3.
Figure 6:
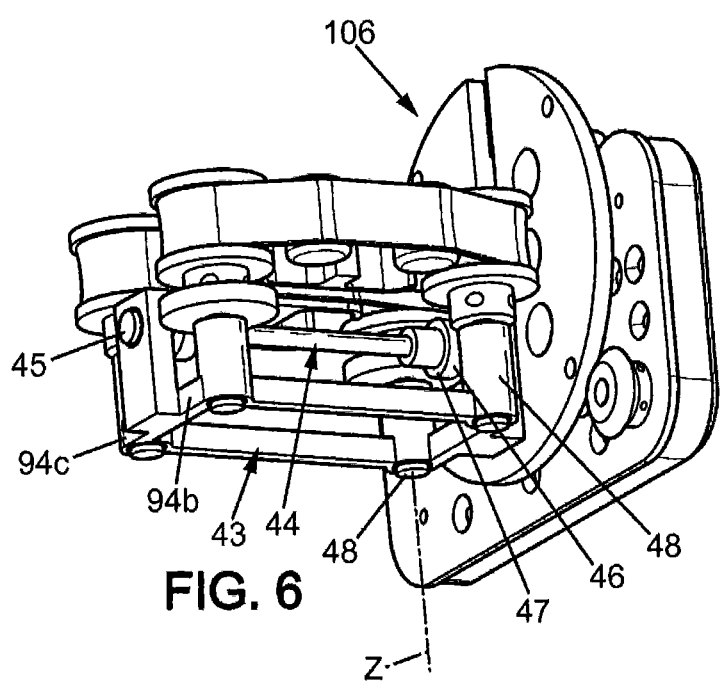
FIG. 6 is a bottom perspective view of the system of FIG. 3.

Referring now to FIGS. 5 and 6, we shall describe a translation driving system 106 for the elongate flexible medical part 6 according to an exemplary embodiment. The translation driving system comprises a frame 43 of the housing 39. The frame 43 comprises an assembly of arms or other structural elements defining hearings for the various drive shafts rotatably supported by the frame. The frame 43 receives a rotation driving system on one side and part of a translation driving system on the other. These two sides are separated along axis 23. On the rotation side, the frame 43 comprises two attachment portions 94b, 94c respectively attached to the attachment areas 93b, 93c described above.

The frame supports a drive shaft 44 via an end bearing 45 and a second end bear in 46 at the opposite end. The drive shaft 44 extends along the main direction, substantially parallel to the axis 23 but offset relative thereto in a transverse direction. It extends between a first end, turning within end bearing 45, and a second end protruding beyond bearing 46. In addition, the shaft 44 comprises at least one gear 47 concentric with the axis of the shaft 44, for rotating a translation drive member 48 of the elongate flexible medical part. In the present example, the translation drive member 48 of the elongate flexible medical part is a shaft mounted on the frame 43 so as to be rotatable about an axis normal to the main direction, meaning the transverse direction. The translation drive member 48 is operatively coupled to an application surface 49 placed in contact with the elongate flexible medical part 6, such that the rotation of the translation drive member 48 about the transverse direction drives the elongate flexible medical part translationally along the axis 23. In the example shown, application surfaces 49 are provided by belts 50 and 51 arranged one on each side of the elongate flexible medical part 6. The belts 50 and 51 are endless belts driven by the rotation of a respective translation drive member 48, 52. For example, a translation drive member 48 is used as described above to drive belt 50, and a similar member 52 is used to drive belt 51. Member 52 is arranged diagonally to member 48 in a rectangle whose other two vertices contain driven pulleys 53 and 54. Thus, on one side the translation drive member 48 and driven pulley 53 receive belt 50. On the other side, the drive member 52 and driven pulley 54 receive belt 51. Translation drive member 52 also cooperates with the shaft 44, via a transfer gear 154 supported by the shaft 44.

As a variant, a system of belts is not necessarily used and there is direct use of the member 18 and a counter-member which are arranged one on each side of the elongate flexible medical part 6 in order to drive the translation.

The main direction 23 was described above as being that of the translation driving axis of the elongate flexible medical part. The transverse direction was defined as the direction of the axis between the level of the shaft 44 and the level of the elongate flexible medical part 6. A third direction can be defined, the lateral direction, forming a trihedron with the two other directions. A lateral movement system 55 may be provided for the elongate flexible medical part 6. For example, a spacer 56 is provided which can be moved laterally and which comprises a contact surface 57 cooperating with an inner face of the belt 49. Moving the spacer 56 in the lateral direction will move the application surface 49 of the belt 50. This clamps the elongate flexible medical part 6 between the two belts and/or shifts the axis along which the elongate flexible medical part extends between the application surfaces relative to axis 23 (while keeping these axes parallel) in order to improve the driving in rotation.

The spacer 56 also comprises a tensioning surface 58 intended for tensioning the belt 50. The spacer 56 comprises for example, in the lateral direction, a front face providing the contact surface 57, and a rear face opposite the front face. The rear face provides the tensioning surface 58, which cooperates with the belt on the return side. Thus, regardless of the lateral offset imposed by the spacer 56 within the dedicated interval, the belt remains tensioned.

On the side opposite the spacer 56 relative to the elongate flexible medical part 6, the lateral movement system 55 comprises a pusher 59. The pusher 59 can be movable in the lateral direction. The pusher 59 comprises a contact surface 60 opposite contact surface 57. The elongate flexible medical part 6 is gripped by the belts 50 and 51 between these two contact surfaces 57 and 60. The lateral offset of the axis of the elongate flexible medical part, imposed by the spacer 56, can cause displacement of the pusher 59 in the lateral direction via the elongate flexible medical part, against a biasing means (not shown).

On this same opposite side, two tensioning pulleys 61 and 62 are provided which, together with the contact surface 60, tension the be 51. The two tensioning pulleys 61 and 62 are mounted to be rotatable about the transverse direction relative to the frame 43.

Thus, as one can see from the above description, installing the elongate flexible medical part 6 within the mobile apparatus comprises placing the elongate flexible medical part 6 between the two belts 50 and 51. The clamping of the elongate flexible medical part 6, and the lateral offset of the axis of the elongate flexible medical part relative to axis 23, are obtained by adjusting the lateral movement system, meaning by adjusting the lateral position of the spacer 56, via an adjustment system that is not shown (for example manually before the procedure).

Once the elongate flexible medical part 6 is in position and clamped, movement of the elongate flexible medical part along the axis 23 is controlled by simple rotation of the drive shaft 44. Rotation of the drive shaft 44 relative to the frame 43 about its axis, parallel to axis 23, causes rotation of at least rotation driving member 48 about its own axis (transverse axis) due to meshing. In practice, in the present case, rotation of the drive shaft 44 relative to the frame 43 about its axis, parallel to axis 23, also causes rotation of rotation driving member 52 about its own axis (transverse axis) due to meshing. Rotation driving member 48 drives belt 50, the application surface thereof then being subjected, at the interaction with the elongate flexible medical part 6, to a translational movement parallel to axis 23. Rotation driving member 52 drives belt 51, the application surface thereof then being subjected, at the interaction with the elongate flexible medical part 6, to a translational movement parallel so axis 23. These two movements are generated in the same translational direction for the application surfaces (in other words, in opposite directions of rotation of the two belts). The movement of the belts drives translation of the elongate flexible medical part.

To generate a translational movement of the elongate flexible medical part 6, it is therefore sufficient to rotate the shaft 44.

However, as the shaft 44 describes a rotation about the axis 23 due to the rotation of the mobile apparatus about this axis, while the translation motor 20 remains fixed relative to the frame, a transfer system 63 needs to be provided which always connects the shaft 44 to the motor 20, regardless of the position of the mobile apparatus 22 relative to this direction. The transfer system 63 comprises a fixed part 64 supported by the base 21, and a mobile part 65 supported by the mobile apparatus 22. A first exemplary embodiment will be given with reference to FIGS. 2 and 3.

According to this first embodiment, the fixed part 64 comprises a belt 66 which is guided along a closed continuous path. A guide is provided for the belt.

Figure 4:
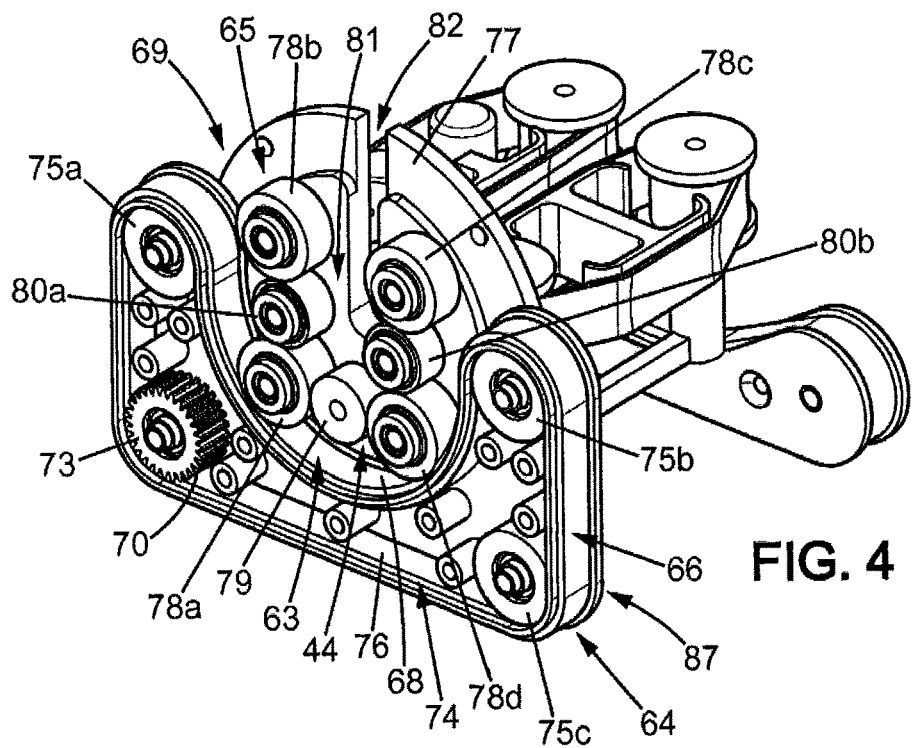
FIG. 4 is a partial view of the system of FIG. 3.

The belt 66 has a portion 68 forming an arc of a circle centered on the axis 23. This arc portion 68 has a minimum central angle, which will be explained in more detail below, and a maximum central angle which is strictly less than 360°. In particular, the belt 66 defines an access aperture 69 that is large enough to allow passage of the elongate flexible medical part 6. In the particular example represented, the arc portion 68 of the belt 66 has a central angle of about 180°. The belt 66 also has a driving portion 70. The driving portion receives the drive command from the translation motor 20. For example, as represented in FIG. 2, the fixed part 64 comprises shaft 71 connected to motor 20, traversing passage 28, and rotating a gear 72 about the vertical axis. Said gear cooperates by conical meshing with a gear 73 having an axis parallel to axis 23. This gear 73 cooperates with the driving portion 70 of the belt as shown in FIG. 4.

The fixed part 64 comprises a set of pulleys adapted to guide the belt 66 so that it moves along a path 74 comprising both the driving portion and the arc portion 68. For example, pulleys 75a, 75b, 75c are provided having parallel axes and arranged to form a rectangle with the gear 73. The path 74 includes three sides of the rectangle, and the arc portion 68 is provided in place of the fourth side. Note that the inner face 76 of the belt 66 is designed to cooperate with the gear 73 to transmit motion via matching shapes, meshing, or other.

The mobile part 65 comprises a support disc 77 integral to the frame 43. The support disc 77, the frame 43, and any other integral part, in particular the housing 39, of the mobile apparatus 22 are generally referred to as a "mounting" 121. The support disc 77 supports a plurality of gears 78a, 78b, 78c, and 78d. These gears 78a-d are each mounted so as to be rotatable relative to the support disc 77 about an axis parallel to the main direction. In addition, these gears 78a-78d are arranged in a circle centered on the axis 23 (therefore concentric with the arc port on 68 of the belt 66). The radius of this circle is smaller than the radius of the arc portion 68 of the belt 66. Each gear 78a-d has its own radius, such that the sum of the radius of the circle and of the radius of the gear 78a-d corresponds to the radius of the arc portion 68 of the belt 66.

Furthermore, each gear 78a-d is in a meshing relation with the shaft 44 passing through the support disc 77. For example, a direct meshing relation may be provided, as is the case for the two gears 78a and 78d which are in direct contact with the head 79 of the shaft 44. There may also be an indirect meshing relation, as is the case for the two gears 78b and 78c which are in contact with the head 79 of the shaft 44 via the two gears 78a and 78d.

A system may also be provided for transferring motion between the "indirect" gears 78b and 78c and the "direct" gears 78a and 78d, so that all they rotate in the same direction. There can thus be an intermediate gear 80a provided between gears 76a and 78b and an intermediate gear 80b provided between gears 78c and 78d.

Figure 17:
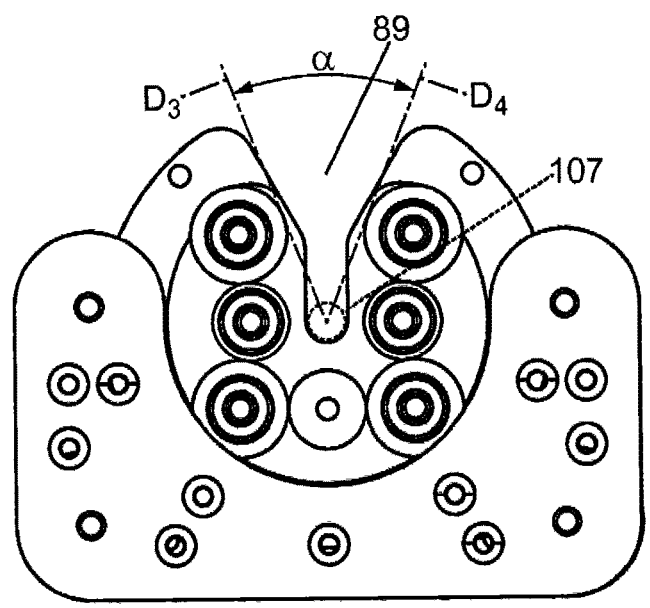
FIG. 17 is a view similar to FIG. 8a for a tenth embodiment.

Thus, the support disc 77 supports a mechanized system 78a-78d, 80a-80b, which has an access aperture 81 aligned with an access aperture 82 of the support disc 77. The access aperture contains a passage region 107 allowing the passage of the elongate flexible medical device during normal operation. The access aperture 81 is defined by two straight lines D3 and D4 which, when projected onto a plane normal to the axis 23, extend from the passage area 107 to each of the adjacent driving surface portions 78b, 78c. The access aperture 81 forms an angle of aperture of at least $\alpha=30°$ or possibly at least 45°. Unlike the example shown, one can minimize the intrusion of the bearing surfaces for movable components, such as the support disc 77 or the covers 84, into the access aperture 81 (such a variant is shown in FIG. 17).

In the present case, the mechanized system has gears arranged in a general U shape, the open side of the U defining the access aperture 81. A first arm of the U comprises aligned gears 78a, 80a, and 78b. A second arm of the U comprises aligned gears 78d, 80b, and 78c. Gears 78a and 78d, are arranged one on each side of the head 76 of the shaft 41 to form the base of the U.

In the position represented in FIG. 4, the gears 78a and 78d, are engaged with the belt 66 in the arc portion 68 of the belt. In this position, to drive the elongate flexible medical part 6 in translation along the axis 23, gear 73 drives the belt 66. The belt 66 rotates gears 78a and 78d about their own axis relative to the support disc 77 (assuming for clarity that the support disc 77 is unmoving during this operation) Gears 78a and 78d rotate the shaft 14 via the head 79. Rotation of the shaft 44 causes translation of the elongate flexible medical hart by the mechanism described above.

Figure 3:
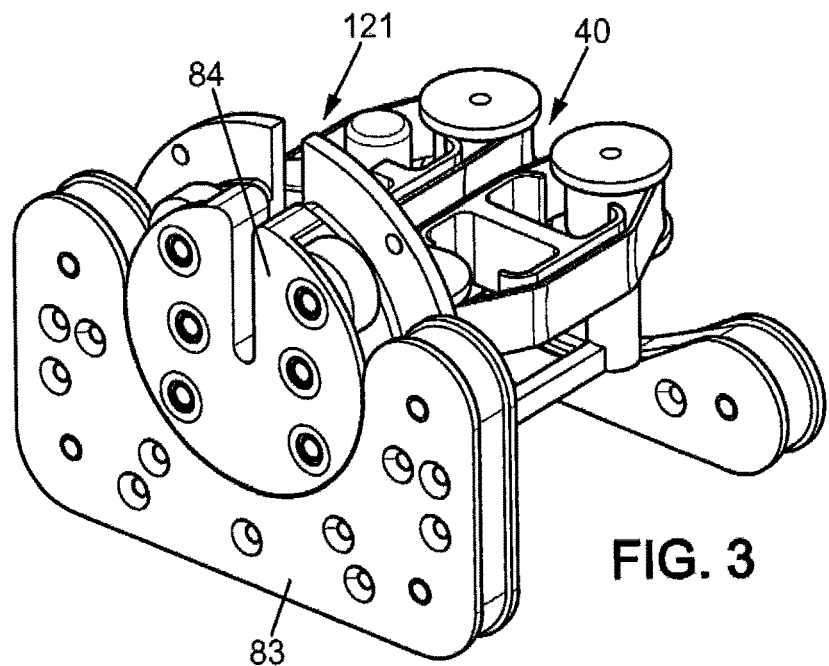
FIG. 3 is a partial view of the system of FIG. 2.

As can be seen in FIG. 3, in actual practice the various mechanisms are hidden and guided by respective covers 83 and 84 for the fixed part and mobile part. The covers have the same access apertures as described above, and define bearings for the shafts of the various gears.

As the inner face 76 of the belt is designed to mesh with gear 73, and the opposite outer face 88 is designed to mesh with gears 78a-d, each is shaped for such meshing, for example by being provided with teeth that fit with the teeth of the various gears.

Figure 8A:
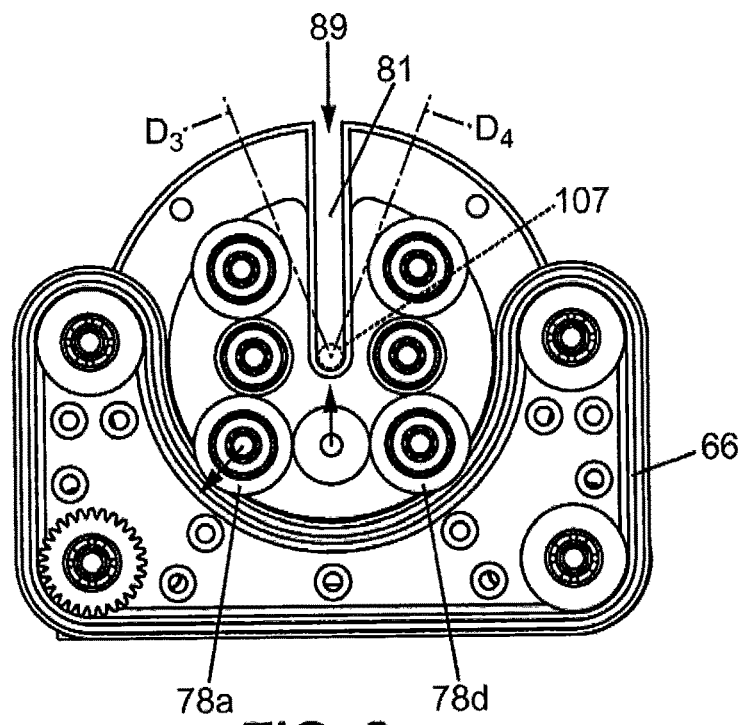

FIG. 8a shows an initial position of the driving module. During a preparatory phase, the single access aperture 89, formed by the various aligned access apertures 93, 81, 82, allows insertion of the elongate flexible medical device into the module, into the inside space 40 in particular between belts 50 and 51. At the rotation driving system the elongate flexible medical part passes through passage region 105, and at the translation driving system the elongate flexible medical part passes through passage region 107.

To generate a pure translational movement, the rotation motor 19 is locked. The translation motor 20 is controlled to generate movement of belt 66 along its path. The arc portion 68 causes gears 78a and 78d to rotate about their axis, which drives the translation of the elongate flexible medical part along axis 23. The elongate flexible medical part 6 can be withdrawn at any time via the access apertures 93, 81 and 82.

To generate a rotational movement, the rotation motor 19 rotates belt 30 which causes the mobile apparatus 22 to rotate about axis 23. The driving surface portions 38a-38d are arranged so that, regardless of the relative orientation of the moving element 22 and the base 21, at least one of these portions 38a-38d is in a cooperative relation with the belt 30. For example, starting from the initial position of FIG. 7, portions 38b and 38c are engaged with the belt 30. When ordering a rotational movement that is clockwise in this figure, portion 38c will gradually disengage from the belt 30 until only portion 38b is transferring motion. Then, portion 38a will start cooperating with the belt 30 as it reaches the position of portion 38b in FIG. 7. The central angle of the arc portion 30' is therefore at least equal to that of the aperture 93. However, it is at most equal to 360° minus the angle of aperture of the aperture 93, to prevent it from being narrower than the aperture 93 itself. During this same movement, gears 78a and 78d roll on belt 66 until one of the gears, here gear 78d, exits the arc portion 68. In addition, it may be desirable to prevent translational movement of the elongate flexible medical part when ordering the rotation. In this case, action is taken so that the relative orientations of the shaft 44 and the elongate flexible medical part 6 within the mobile apparatus remain unchanged (meaning that the shaft 44 is not rotated relative to the frame 43). This can be achieved by controlling the translation motor so that the belt 66 travels a corresponding distance to prevent any rotation of gears 78a-d relative to the support disc 77.

Figure 8B:
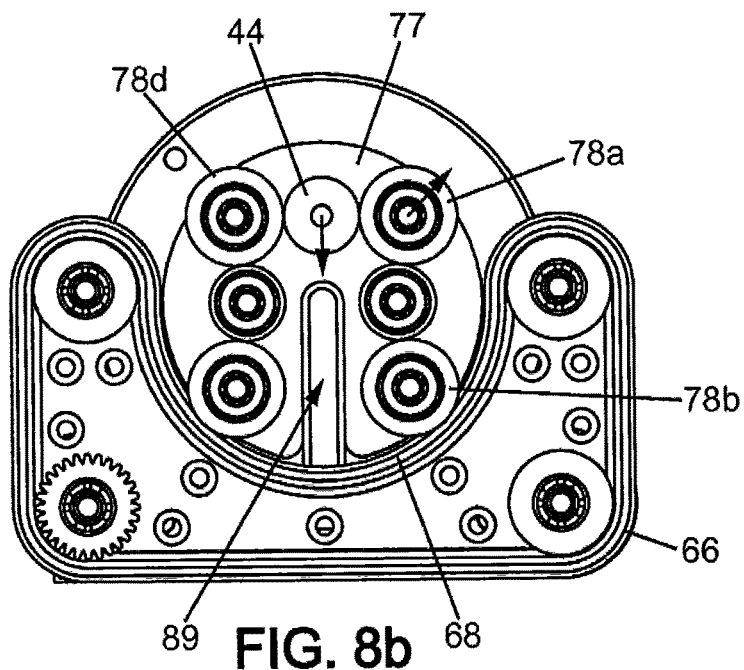
Figure 8C:
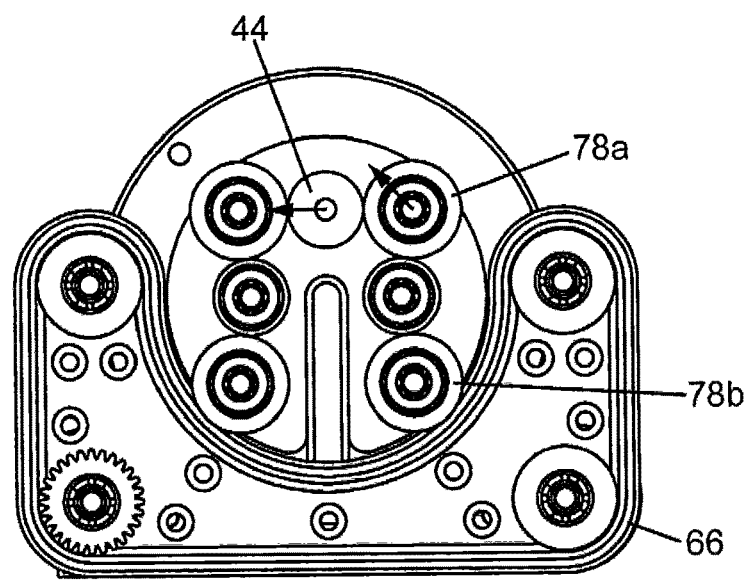

This is particularly clear when one compares FIGS. 8a and 8b, where arrows have been added to the various moving components to illustrate their relative orientations in the different positions.

Thus, if the operator wants to obtain a pure rotational movement of the elongate flexible member medical 6, the two motors 19 and 20 are controlled at predetermined ratios.

During rotation of the mobile apparatus 22, the elongate flexible medical part 6 remains captured between belts 50 and 51 from which it receives the rotational motion imparted to the mobile apparatus.

Of course, it could be arranged so that simultaneous translation and rotation of the elongate flexible member medical 6 is ordered, in which case only the rotation motor 19 may be controlled, or the two motors 19 and 20 may be controlled according to a ratio other than the predetermined ratio for pure rotation.

As can be seen in FIG. 8b, in this position it is not possible to withdraw the elongate flexible medical part 6 via the access apertures 89, 93, because these apertures are respectively obstructed by belt 66 and belt 30 of the fixed part. However, there remains one access aperture 89. To remove the elongate flexible medical part 6 from the module when in this position, the rotation motor is controlled to achieve a rotational movement in the appropriate direction, for example towards the position of FIG. 8a. If it is desired to withdraw the elongate flexible medical part 6 from the module with no translational movement of the member within the patient, the translation motor is also controlled according to the predetermined ratio, in order to generate pure rotational movement.

If, in the position of FIG. 8b, translation of the elongate flexible medical part 6 is desired, the rotation motor 19 is locked and the translation motor 20 is controlled as explained above. In the position represented, the arc portion 68 of the belt 66 causes rotation of gear 78a and gear 78b, but no longer that of gear 78d as above. Regardless of the relative orientation of the mobile apparatus 22 and the base 21, at least one gear 78a-d is in a driving relation with the arc portion 68 of the belt 66. This property defines the minimum central angle of the arc portion 68 of the belt 66, based on the number and arrangement of gears 78a-78d. In the square configuration shown, the minimum central angle of the arc portion 68 of the belt 66 is at least 90°. In the example presented, 180° is used for clarity.

The following figures represent other embodiments. These embodiments are not represented in full, and primarily show the portion which replaces the plate 90 or belt 30 as appropriate.

Figure 9:
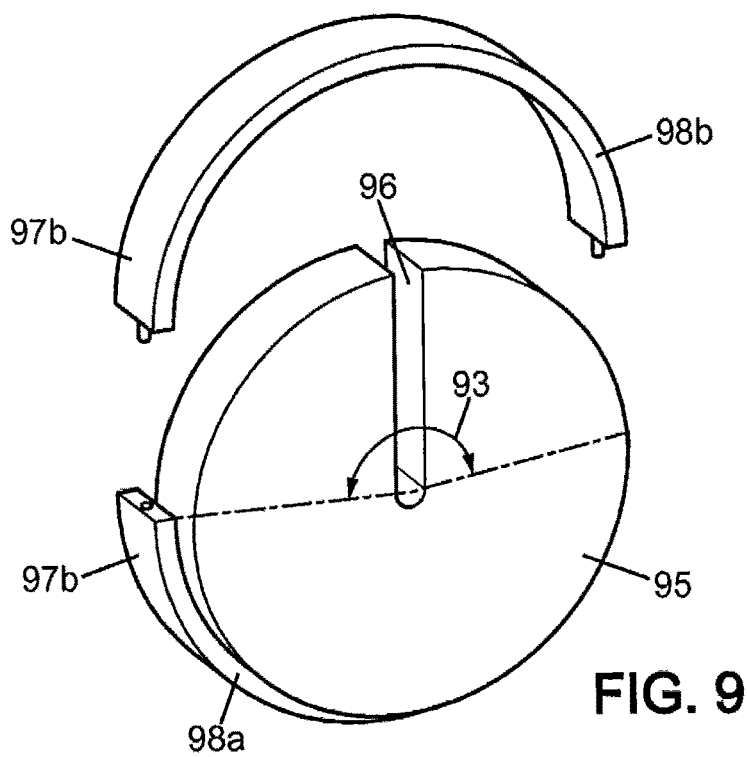
FIGS. 9 to 13 are partial perspective rear views of the second to sixth embodiments respectively.

FIG. 9 thus represents a second embodiment. A distinctive feature of this embodiment is that it provides two different configurations, an access configuration and driving configuration. The plate 90 is replaced by a disc 95 having an access aperture 96 communicating with the inside space 40. The access aperture 96 has any desired angle of aperture. The disc 95 has no driving portion. A driving ring 97 is attached to the disc 95, for example by clamping. The ring 97 comprises an outer peripheral surface 97b intended to engage the belt 30. The ring 97 is made of two portions 98a and 98b that are detachable from each other. For example, a first portion 98a, fixed on the disk 95, does not obstruct the access aperture 96. A second portion 98b is associated with the first portion 98a in a driving configuration. In said driving configuration, the second portion 98b is obstructing the access aperture 96. 'Obstructing' the access aperture is understood to mean that a catheter cannot be radially inserted into/withdrawn from the inside space 40 via the access aperture. One can thus consider this second portion 98b as forming a plug. The association of the second portion 98b and first portion 98a is done in a detachable manner by any suitable means, for example a snap-fit association. In the access configuration (represented) where the two portions are not assembled, both ends of portion 98a define an access aperture 93 where the angle of aperture is at least 30°, and may be on the order of 180°, as shown, or possibly more.

Thus, when one wishes to withdraw the flexible elongate medical part, one simply removes the removable portion of the driving ring to allow access to the inside space via the access aperture. In the usage configuration, the driving surface is continuous over 360°, guaranteeing proper driving action.

Figure 16:
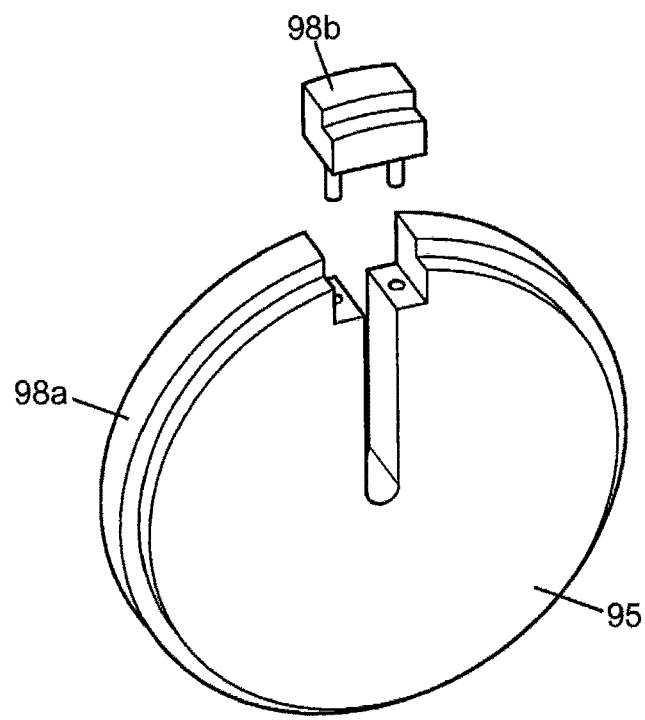
FIGS. 15 and 16 are partial perspective rear views of an eighth and ninth embodiment respectively.

Alternatively, as shown in FIG. 16, the second portion 98b need not be fixed directly to the first portion, but instead to the plate 95 itself. As can be seen in this figure, in this embodiment the angle of aperture of the access aperture 93 can be small.

Figure 10:
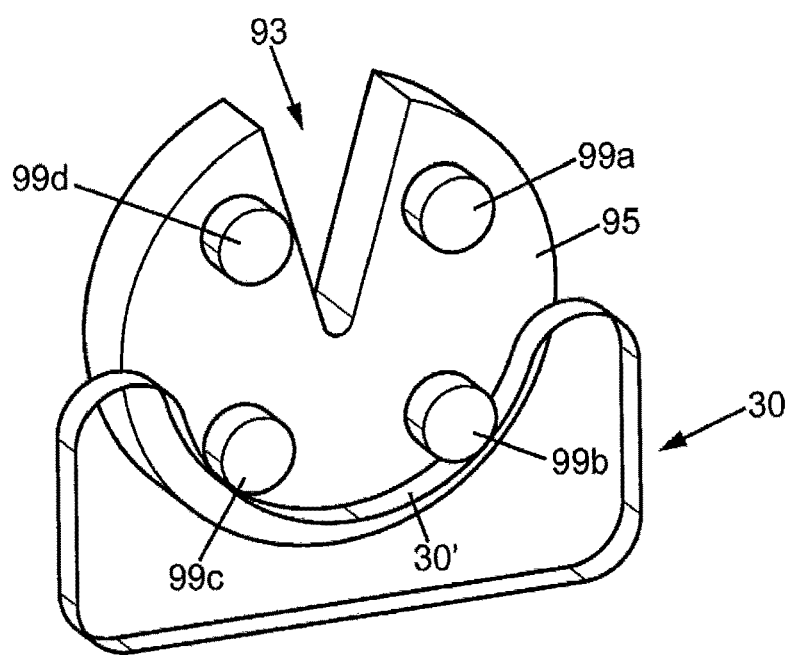

Alternatively, as shown in FIG. 10, a belt 30 having a large radius of curvature in its arc portion 30' is not necessarily used. The plate 95 carries four rollers 99a-99d whose centers are arranged in a circle centered on the axis 23. Each roller has its own radius, such that the sum of this radius and that of the above circle corresponds to the radius of the circle of the arc portion 30' of the belt 30. Two rollers 99a and 99d arranged one on either side of the access aperture 93 are spaced apart by an angle of aperture at least equal at 30° but not too large to ensure that at least one of the rollers always engages with the belt 30, regardless of the relative orientation of the base 21 and the mobile apparatus 22.

Figure 7:
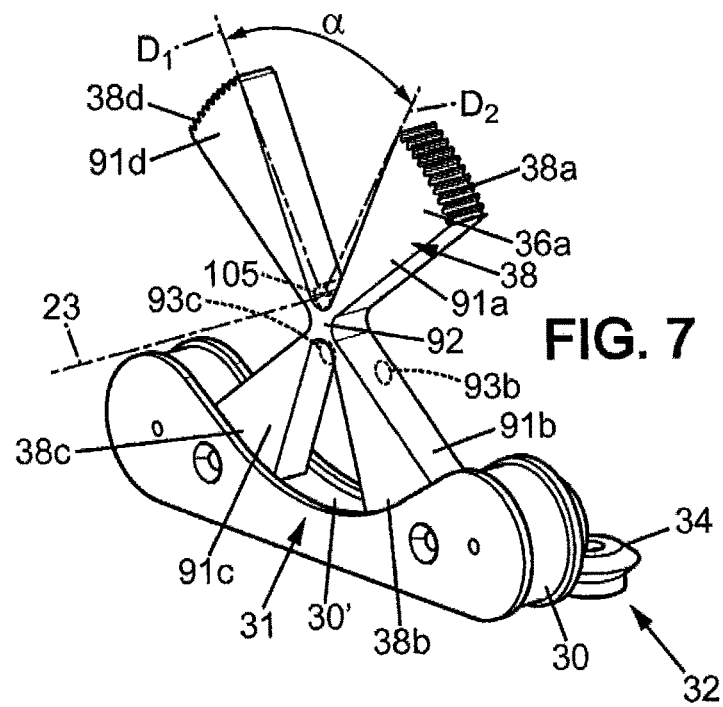
FIG. 7 is a rear perspective view of the system of FIG. 2, FIGS. 8a, 8b, and 8c are front views of the system of FIG. 3, in different driving configurations.
Figure 11:
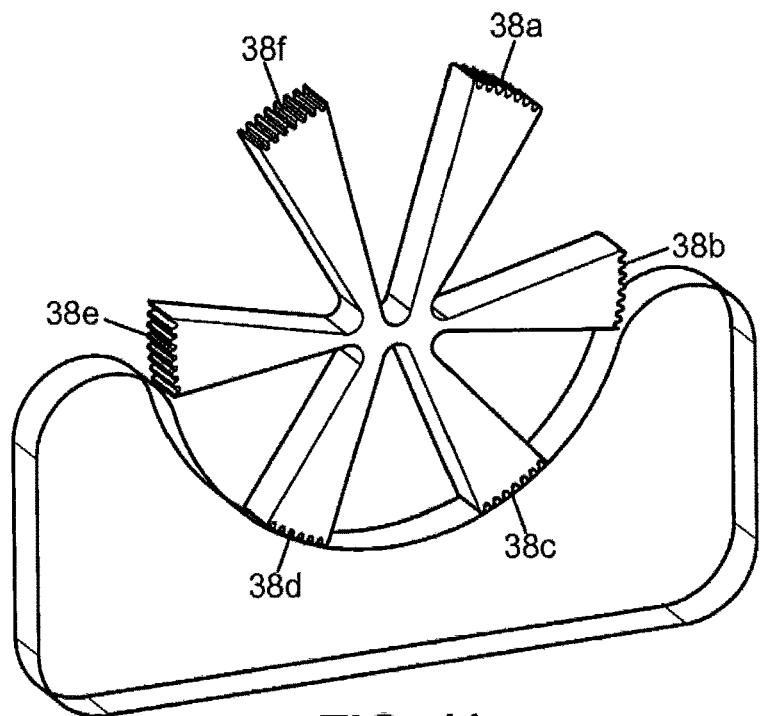

FIG. 11 shows a variant of FIG. 7, with six driving portions 38a-38f instead of four.

Figure 12:
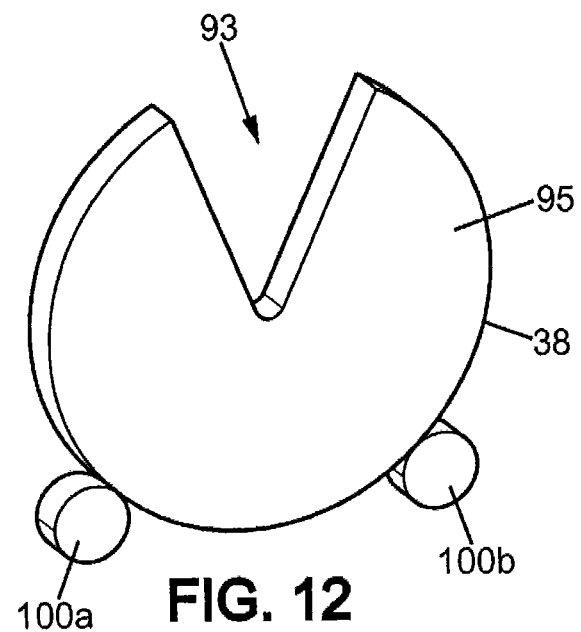

The embodiment of FIG. 12 differs from the above embodiments in that a belt 30 is no longer used. Said belt is replaced by two distinct rotation control members 100*a*, 100*b*, possibly with one dependent, on the other. These two members 100*a*, 100*b* are, for example, small friction rollers rotated either directly or indirectly by gear 35. The plate 95 comprises a peripheral driving surface 38 cooperating with the two rollers 100*a* and 100*b*. An access aperture 93 having a wide angle of aperture allows removal/insertion of the catheter. The angular distance between the rollers 100*a*, 100*b*, as observed from the axis 23, is greater than the angle of aperture of the access aperture 93. Thus, regardless of the relative orientation of the mobile apparatus 22 and the base 21, at least one of the rollers 100*a*, 100*b* is in contact with the driving surface 38, particularly when the other roller is facing the access aperture 93.

Figure 13:
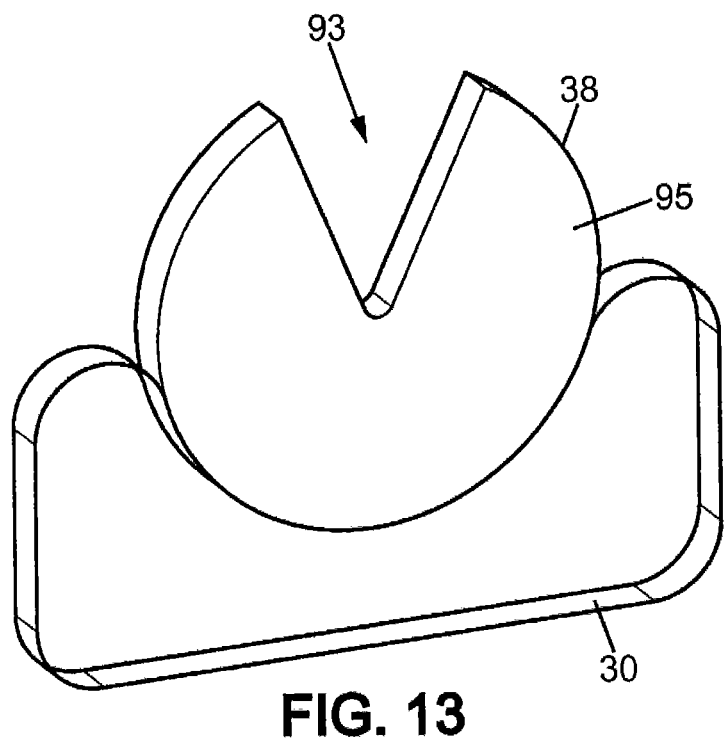

In yet another embodiment, as represented in FIG. 13 and described with reference to the embodiment of FIG. 12, the two rollers 100*a* and 100*b* are replaced by a belt 30. The angle of aperture of the arc portion of the belt 30 is greater than the angle of aperture of the access aperture 93. Thus, regardless of the relative orientation of the mobile apparatus 22 and the base 21, a portion of the belt 30 is in contact with the driving surface 38.

Figure 14A:
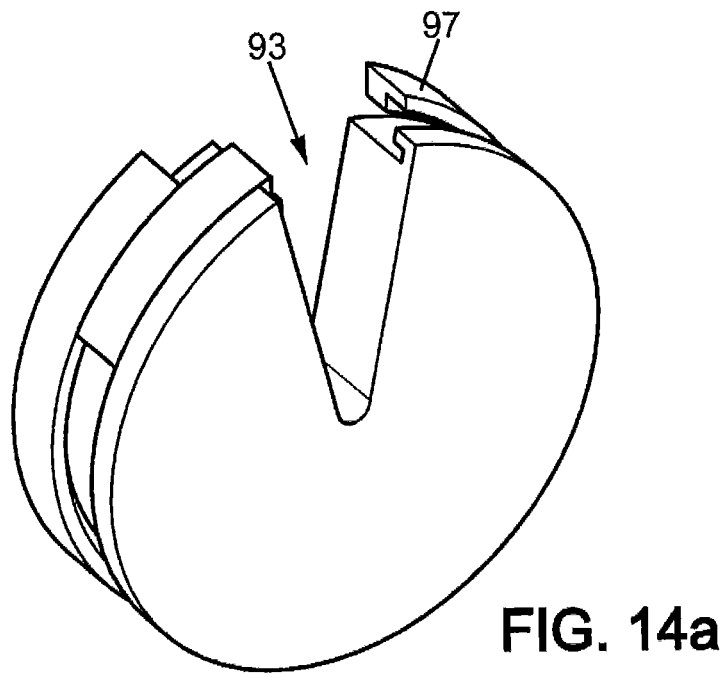
FIGS. 14a and 14b are views similar to FIG. 9 for a seventh embodiment in two different configurations.
Figure 14B:
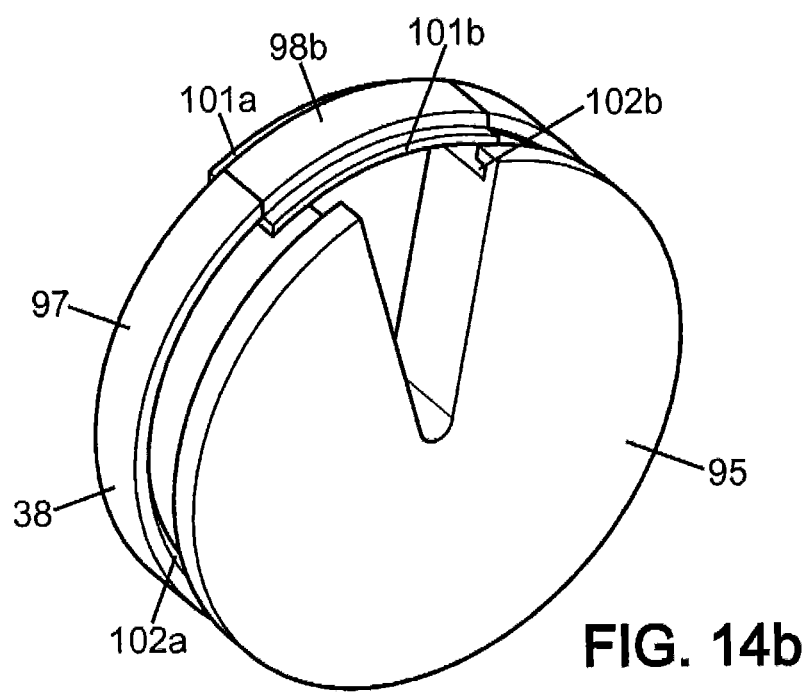

The embodiment of FIGS. 14*a* and 14*b* reuses the principle of a ring 97 that can be placed in two configurations: a driving configuration (FIG. 14*b*) where it provides a closed peripheral driving surface 38, and an access configuration (FIG. 14*a*) where it provides a wide access aperture 93. One difference from the embodiment of FIG. 9 is that portion 98*b* of the ring, alternately obstructing or allowing radial access to the catheter, is not completely removable and remains assembled to portion 98*a* in the access configuration. Portion 98*b* may thus have two edges 101*a*, 101*b* projecting axially relative to the main body of portion 98*b*, each retained in a groove 102*a*, 102*b* forming respective tracks for portion 98*a*. of the plate 95 in the access configuration.

One will note that such an obstructive system could possibly be used to alternate between obstructing and allowing access to the inside space elsewhere than in the rotation driving system, for example in the translation driving system.

Figure 15:
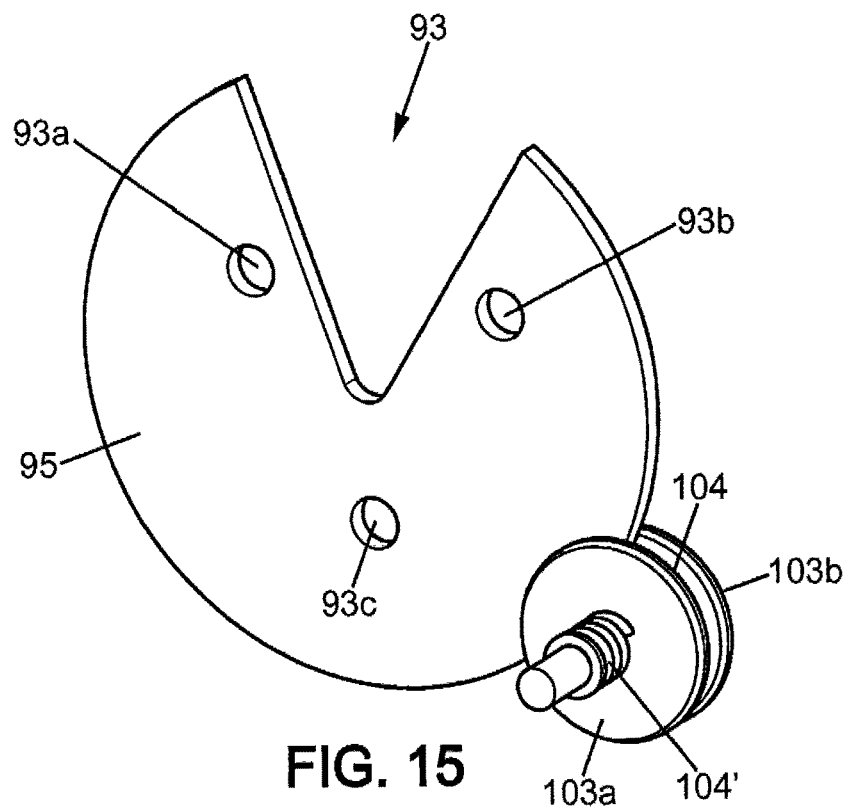

FIG. 15 shows an embodiment offering an alternative to the belt 30 or rollers 100*a*, 100*b*. Two discs 103*a*, 103*b* are provided, each axially offset to define a slot 104 therebetween into which disc 95 is inserted. The two discs 103*a* and 103*b* are concentric, and can be rotated by gear 35. A spring 104' biases them toward one another. The friction of their rotation about the axis of gear 35 drives the rotation of disc 95 about axis 23. If the access aperture 93 is wide as shown, another disk system 103*a* and 103*b* may be used elsewhere (not shown), as was done with the rollers 100*a* and 100*b*. The areas 93*a-c* of attachment to the frame are identified.

Figure 18:
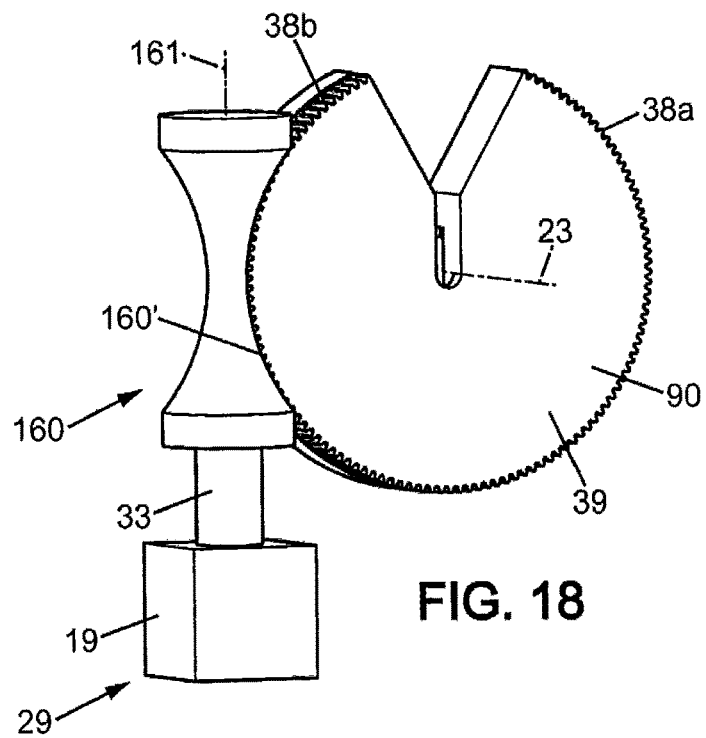
FIG. 18 is a partial perspective rear view of an eleventh embodiment.

As a variant, an embodiment may be provided for a rotational control system 29 using a double enveloping worm gear 160, as shown in FIG. 18. According to this embodiment, the rotational control system 29 comprises a double enveloping worm 160 rotated about an axis of rotation 161. The worm 160 comprises, in a cross-section along a plane normal to the axis of rotation 23, a continuous driving surface in the shape of an arc 160' of a circle whose center coincides with axis 23.

The plate 90 comprises, for example, separate driving surface portions 38*a-b* a right circular cylinder about the axis 23, cooperating with the double enveloping worm 160 and forming a rotation driving system 38. For this cooperation, it may be arranged for example that the double enveloping worm 160 has a driving face, and that the discrete driving surface portions 38*a-b* have a complementary surface. The driving face of said worm and a driving surface portion 38*a-b* are in a driving relation such that rotation of the worm 160 about its axis of rotation causes rotation of the frame 39 about the axis 23.

The angular distance of the driving surface 160 is greater than the angle of aperture of the access aperture, and less than 360° minus the angle of aperture of the access aperture.

Figure 19:
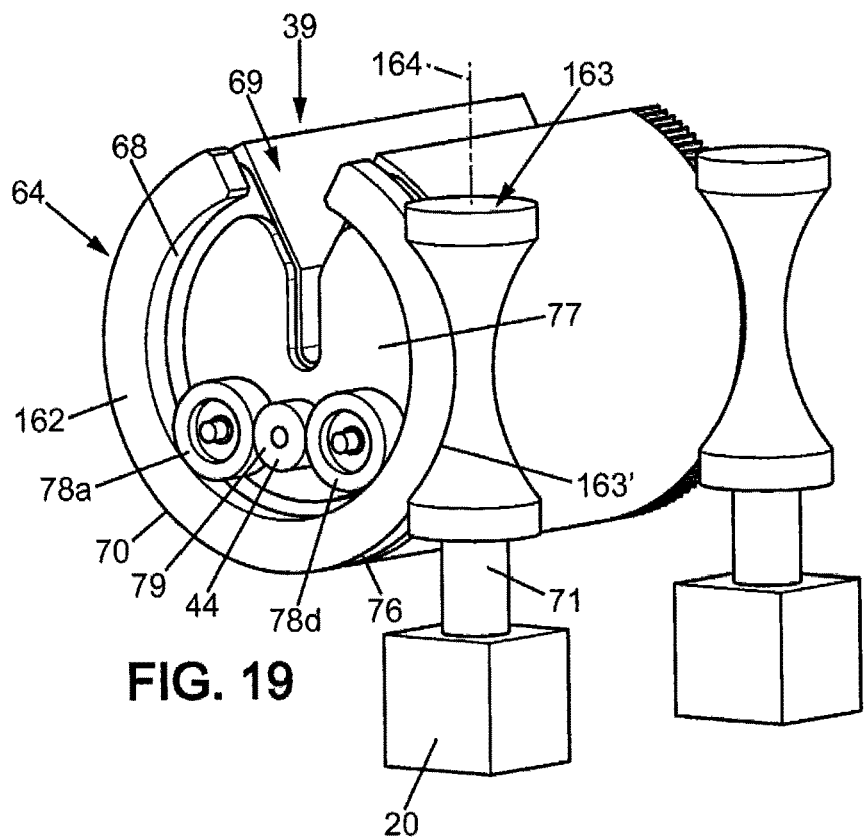
FIG. 19 is a partial perspective front view of a twelfth embodiment.

As a variant, an embodiment may be provided for a translational control system using a double enveloping worm gear 163, as shown in FIG. 19.

According to that example, the fixed part 64 comprises a partial ring 162 which is rotatable about the axis 23 independently of the frame 39.

The partial ring 162 defines an arc portion 68 of a circle centered on the axis 23. The arc portion 68 has a minimum central angle and a maximum central angle which is strictly less than 360°. In particular, the partial ring 162 defines an access aperture 69 that is large enough to allow the passage of the elongate flexible medical part 6. In the particular example represented, the arc portion 68 of the partial ring 162 has a central angle of 300°. The partial ring 162 also has a driving portion 70. The driving portion 70 receives the drive command from the translation motor 20. For example, as represented in FIG. 19, the fixed part 61 comprises the shaft 71 connected to the motor 20, passing through the passage 28, and rotating the worm 163 about a vertical axis 164. The worm 163 comprises, in a cross-section along a plane normal to the axis of rotation 23, a continuous driving surface in the shape of an arc 163' of a circle whose center coincides with axis 23.

The double enveloping worm 163 cooperates by meshing with the partial ring 162.

The central angle of the driving surface 163' is greater than the angle of aperture of the access aperture 69 of the partial ring 162 and less than 360° minus the angle of aperture of the access aperture.

One will note that the outer face 76 of the partial ring 162 is designed to cooperate with the double enveloping worm 163 to transmit motion via matching shapes, meshing, or other.

The mobile part 65 comprises the support disc 77. The support disc 77 supports a plurality of gears 78*a* and 78*d*. These gears 78*a-d* are each mounted relative to the support disc 77 so as to be rotatable about an axis parallel to the main direction. In addition, these gears 78*a*-78*d* are arranged in a circle centered on the axis 23 (therefore concentric with the arc portion 68 of the partial ring 162).

Furthermore, each gear 78*a-d* is in a direct meshing relation with the shaft 44.

In the position represented in FIG. 19, the gears 78*a* and 78*d* are engaged with the partial ring 162, in the arc portion 68 of the partial ring 162. In this position, in order to drive the elongate flexible medical part 6 in translation along the axis 23, the double enveloping worm 163 drives the partial ring 162. The partial ring 162 still directly rotates at least one of the gears 78*a* and 78*d* about its own axis relative to the support disc 77 (assuming for clarity that the support disc 77 is unmoving during this operation). Gears 78*a* and 78*d* rotate the shaft 44 by means of the head 79. Rotation of the shaft 44 causes translation of the elongate flexible medical part by the mechanism described above.

Note that, according to one embodiment, as represented in particular in FIG. 19, a double enveloping worm 160 can to used to drive the rotation, and a double enveloping worm 163 can be used to drive the translation, the worms being mounted parallel to each other along respective axes 163, 161 tangential a circle centered on axis 23.

The invention claimed is:

1. The driving module for driving an elongate medical part along an elongation axis, for a robotic system, wherein the driving module comprises:
a base, carrying at least one rotation control member,
a mobile apparatus mounted so as to rotate relative to the base about an axis of rotation, and defining a receiving space for the elongate medical part,
the mobile apparatus comprising a rotation driving system adapted to cooperate with at least one rotation control member, regardless of the relative orientation of the mobile apparatus and the base about the axis of rotation,
the mobile apparatus comprises a removable cap that is suitable:
in the assembled position, for closing an access aperture to the receiving space and for preventing radial movement of the elongate medical part between its usage configuration and its external configuration, and
in the disassembled position, for opening the access aperture and enabling such movement.

2. The driving module according to claim 1, wherein the cap supports a portion of the rotation driving system.

3. The driving module according to claim 1, wherein the a rotation driving system comprises a passage region for the elongate medical part corresponding to the location for the passage of the elongate medical part through the mobile apparatus, and a plurality of rotation driving portions distributed about the axis of rotation, each suitable for cooperating with at least one rotation control member, the rotation driving portions being arranged, in a driving configuration, such that at least one of the rotation driving portions cooperates with at least one of the rotation control member of the relative orientation of the mobile apparatus and the base about the axis of rotation,
an access aperture extending from the receiving space between two adjacent rotation driving portions.

4. The driving module according to claim 3, wherein the access aperture has an angle of aperture of at least 30° measured as projected onto a plane normal to the axis of rotation between two straight lines extending from the passage region to each of the two adjacent driving portions in the access configuration.

5. The driving module according to claim 1, further comprising a translation driving system for the elongate medical part, carried by the mobile apparatus, comprising at least one surface suitable for being placed in contact with the elongate medical part and suitable for being placed in motion relative to the mobile apparatus in order to drive the elongate medical part in translation along the elongation axis,
said surface being further adapted for gripping the elongate medical part so as to rotate it about the axis of rotation.

6. The driving module according to claim 5, wherein the mobile apparatus comprises a frame supporting at least one rotary member of the translation driving system, the rotation driving system being integral with the frame.

7. The driving module according to claim 6, wherein the access aperture is a first access aperture, wherein the frame carries the translation driving system, the translation driving system comprising a passage region for the elongate medical part corresponding to the location for the passage of the elongate medical part through the mobile apparatus, and a plurality of translation driving portions distributed about the axis of rotation, each adapted to cooperate with at least one translation control member of the base,
the translation driving portions being arranged, in the driving configuration, such that at least one of the translation driving portions cooperates with at least one of the translation control members regardless of the relative orientation of the mobile apparatus and the base about the axis of rotation,
a second access aperture extending from the receiving space between two adjacent translation driving portions,
the second access aperture having an angle of aperture of at least 30° measured as projected onto a plane normal to the axis of rotation between two straight lines extending from the passage region to each of two adjacent driving portions in the access configuration.

8. The driving module according to claim 7, wherein the first and second access apertures are superimposed in a projection normal to the axis of rotation, regardless of the relative orientation of the mobile apparatus and the base.

9. The driving module according to claim 5, wherein the cap is suitable for closing and opening an access aperture to the receiving space at the translation driving system.

10. The driving module according to claim 1, wherein the rotation driving system comprises a connection portion and at least two arms extending to either side of the receiving space and each connected to the connection portion.

11. The driving module according to claim 1, wherein at least one, possibly each, of the access apertures has an angle of aperture at least equal to 45° in the access configuration, or possibly at least equal to 90°.

12. Driving module according to claim 1, wherein the rotation control member comprises a belt that can be driven to travel a path along the base, said path comprising an arc portion of a circle centered on the axis of rotation and having a central angle greater than the angle of aperture and less than 360° minus the angle of aperture.

13. The driving module according to claim 1, wherein the removable cap comprises a rotation driving surface that is suitable, in the assembled position, for cooperating with at least one rotation control member in the driving configuration.

14. The driving module according to claim 1, wherein the cap is retained on the mobile apparatus such that it is movable between the assembled configuration and the disassembled configuration.

* * * * *